United States Patent
Shesol et al.

(10) Patent No.: US 6,512,159 B1
(45) Date of Patent: Jan. 28, 2003

(54) FACIAL WOUND DRESSING SUPPORT DEVICE

(76) Inventors: Barry F. Shesol, 18158 E. Long Ave., Aurora, CO (US) 80016; Paul C. Zwiebel, 206 E. County Line Rd. #210, Highlands Ranch, CO (US) 80126

( * ) Notice: Subject to any disclaimer, the term of this patent is extended or adjusted under 35 U.S.C. 154(b) by 39 days.

(21) Appl. No.: 09/708,297

(22) Filed: Nov. 9, 2000

(51) Int. Cl.$^7$ .................................................. A61F 13/12
(52) U.S. Cl. ..................... 602/41; 128/857; 128/888; 2/9
(58) Field of Search .................... 602/41, 60, 61, 602/74, 75; 2/9, 424; 128/857, 858–859, 888; 606/204.15

(56) References Cited

U.S. PATENT DOCUMENTS

| | | | | |
|---|---|---|---|---|
| 1,023,358 A | * | 4/1912 | Bender | 606/204.35 |
| 3,804,087 A | * | 4/1974 | Sarnoff | 602/74 |
| 5,031,609 A | * | 7/1991 | Fye | 128/857 |
| 5,961,479 A | * | 10/1999 | Reeves et al. | 602/41 |
| 5,994,612 A | * | 11/1999 | Watkins | 2/69 |
| 6,039,710 A | * | 3/2000 | Kelley et al. | 128/857 |

* cited by examiner

*Primary Examiner*—Michael A. Brown
*Assistant Examiner*—Quang D Thanh
(74) *Attorney, Agent, or Firm*—Edwin H. Crabtree; Ramon L. Pizavvo; Donald W. Margolis

(57) ABSTRACT

A facial wound dressing support device configured to accommodate a variety of facial injuries and expedites the healing process while minimizing the patient's discomfort. As facial tissue has a high degree of sensitivity and is cosmetically significant, rapid healing with minimal permanent damage is highly desired. The subject wound dressing support device includes a facial mask made of a loose weave "loop like", stretchable, breathable, washable and reusable material. The mask is adaptable to a multiplicity of differing facial topography structures on the head and face of the patient. The mask includes releasable hook fasteners at a first end of the mask which engage the loose weave material at various locations along a length of a second end the mask for securing the mask around the patient's head and next to the patient's face. The facial wound dressing support system may include openings for the patient's eyes, mouth and nose to facilitate continuous use by the patient. The mask also includes a support strap attached to a bottom portion of the mask for holding the mask next to a patient's nose or next to a patient's chin.

10 Claims, 3 Drawing Sheets

FACIAL WOUND DRESSING SUPPORT DEVICE

BACKGROUND OF THE INVENTION (a) Field of the Invention

The present invention relates generally to devices that are worn around the contour of a person's face for the purpose of facilitating healing of facial structures. More particularly this invention relates to a series of facial masks that conform to facial structural contours to retain wound dressings, absorb drainage, compress tissue, protect tissue, and support anatomical structures.

(b) Discussion of Prior Art

The facial tissue area presents a number of unique challenges in facilitating the support required to aid in healing. Due to the complexity of the healing process following facial surgery or injury, the success of the wound dressing can be a critical factor in the successful termination of the healing process. Wound dressings function as follows:

a. a protective barrier against outside environment infection.
b. to compress swollen tissues.
c. function to absorb wound byproducts that tend to accumulate and complicate healing.
d. protects healing tissue from outside physical damage.
e. physical support for damaged anatomical structures.
f. may have value as an acceptable camouflage for unsightly wound appearances.
g. serve to form an occlusive barrier to provide an optimal environment for certain wound types.

The wound dressing is most often secured in place by the application of an adhesive to the skin. This method of dressing fixation has a number of particular drawbacks when applied to the facial area causing difficulty in the healing process, increased patient dissatisfaction, and inconvenience in use and application:

a. difficulty with conforming to the multiplicity of facial contours and asymmetric topography of the facial area that can differ greatly from individual to individual.
b. increased sensitivity of facial skin adds to the incidence of allergic reactions, such as blister formation, rashes, weeping wounds, scars, and permanent pigmentation problems from the conventional wound dressing adhesive that physically stabilizes the dressing retention device.
c. the delicate nature of facial skin increases the susceptibility damage from the stress imparted to the skin at the adhesive attachment point for the wound dressing retention device.
d. inability to adhere in areas of raw, open wounds, or wounds with vulnerable scab formation.
e. lack of satisfactory adherence in hair bearing areas or areas of hypersensitivity.
f. pain associated with adhesive removal in hair bearing areas or areas of hypersensitivity.
g. an adhesive system is not reusable when loosened by movement from the mouth, eyes, nose, and ears, or moisture, thus necessitating reapplication.
h. requirement to individually customize the dressing support device due to the infinite combination of eye, ear, nose, and mouth opening locations precludes economical standardization of facial dressing support devices.
i. facial skin is highly vascular increasing the sensitivity to wound byproducts wherein the desired absorption of the byproducts is difficult due to concave portions of the facial topography precluding direct contact with an absorptive material.
j. prior facial dressing support devices effectiveness is subordinated to the patient needs of speaking, eating, seeing, smelling, and hearing.
k. lack of usefulness in treating a portion of the facial area while not compromising the untreated facial areas.
l. possibly the most important of issues is that a wound dressing, if not properly chosen, can significantly retard and limit wound healing.

The prior art does not disclose the unique structure and advantages of the subject invention as described herein when addressing the need of improved facial wound debridement and enhanced facial wound healing.

SUMMARY OF THE INVENTION

In view of the foregoing, it is a primary object of the present invention to provide a new and useful facial wound dressing support device configured to accommodate a variety of facial tissue injuries that expedites the healing process while minimizing the patient's discomfort.

Another object of the invention is to provide a dressing support device that eliminates the need of adhesive which causes pain during removal, possible allergic reactions, and flimsy application due to hair, moisture, and wound complications.

Still another object of the subject facial wound dressing support device is that the device is made of a stretchable material that can conform to the differing asymmetric topography of an individual's facial structure. This feature allows the material to stay in close contact with damaged facial tissue, thus facilitating timely healing.

Yet another object of the facial dressing support device is that the mask is provided with releasable hook and/or loop fasteners that attach at the rear and top of the head to secure the mask around the head of the patient. These fasteners allow for easy and quick application and removal of the mask to replace wound dressings.

A further object of the invention is to minimize patient discomfort by allowing full facial movement for speaking, eating, smelling, seeing and hearing while the mask is being worn. This is accomplished by using a lightweight stretchable material that has openings for the patient's eyes, nose, and mouth.

The subject wound dressing support device includes a facial mask made of loose weave stretchable material. The mask is adaptable to a multiplicity of differing facial topographies with releasable hook fasteners for securing the mask on the patient's head and face. The facial wound dressing support device may include openings for the patient's eyes, mouth and nose to facilitate continuous use by the patient. The facial wound dressing support device can be configured into a number of different shapes to; cover the damaged portion of the facial area, such as the peri-orbital region, the peri-oral region and full face coverage if required, or the face in toto. The loose weave stretchable material of the mask construction conforms to the patient's head and face thus remaining in close contact with the facial tissue. This material has the ability to absorb wound drainage, retain a wound dressing medium, support damaged tissue, provide physical protection or releasably secure the hook fasteners.

These and other objects of the present invention will become apparent to those familiar with various types of dressing devices from the following detailed description, showing novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principals thereof, and in which.

DESCRIPTION OF THE PREFERRED EMBODIMENTS

Figure 1:
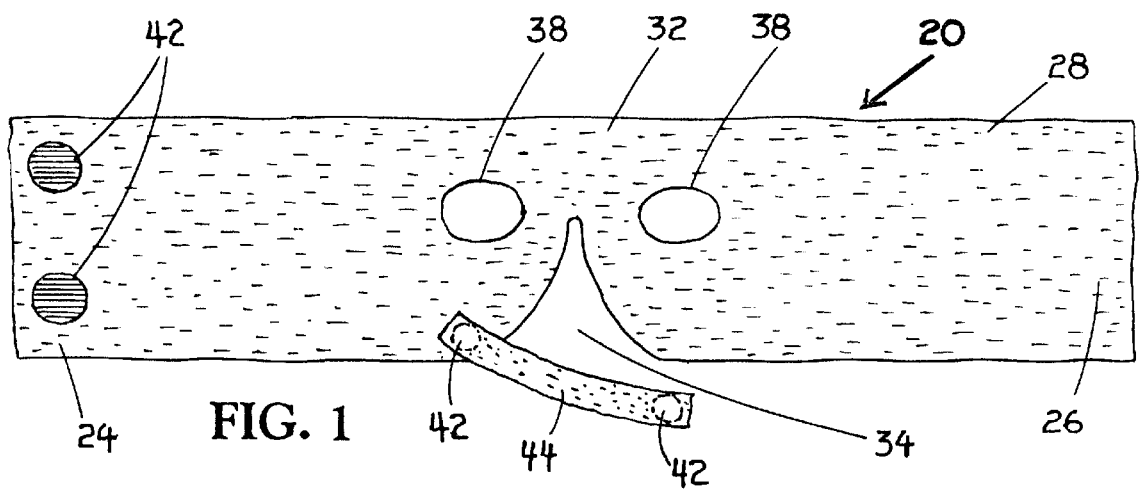
FIG. 1 is a flat pattern layout of a peri-orbital mask with a securing strap disconnected at one end ready for attachment on the patient. A left end of the mask shows two round hook fasteners that attach to loose weave material at a right end of the mask when the mask is secured around a patient's head. A center section of the mask has openings for the eyes and nose.

In FIG. 1, a flat pattern layout of a peri-orbital mask is shown having general reference 20. The mask 20 is used for receipt around a patient's head 22. The patient's head 22 is shown in FIGS. 2–5, 7–11 and 13–16.

Figure 5:
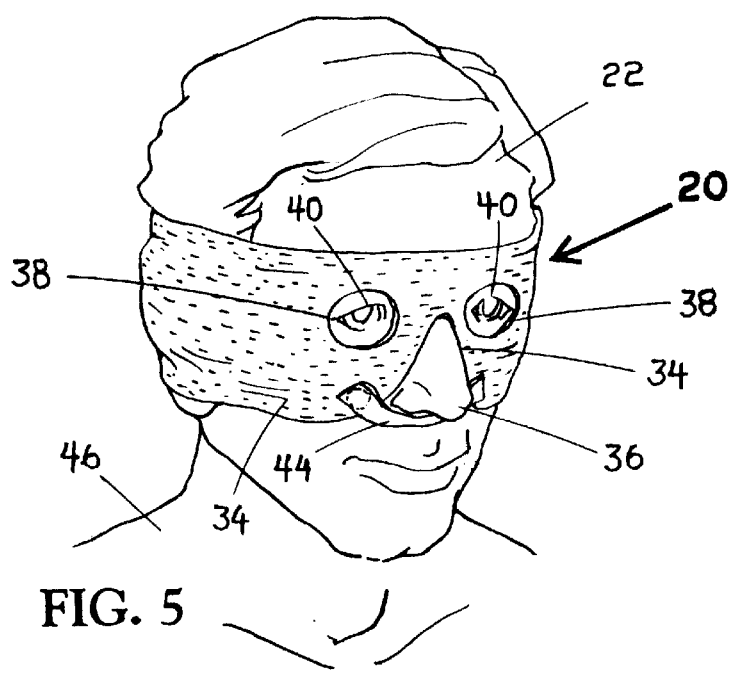
FIG. 5 is a perspective view the peri-orbital mask of FIG. 1 in use and fully attached to the patient with the securing strap in place.
Figure 3:
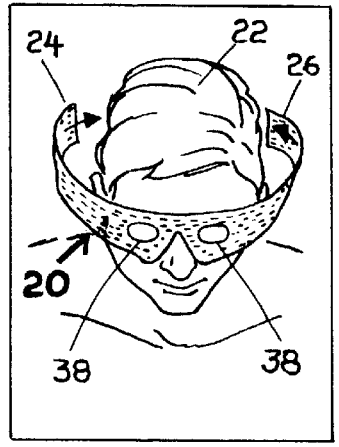
FIG. 3 shows the installation of the peri-orbital mask around the patient's head with the ends of the mask positioned to attach at the rear of the patient's head.
Figure 4:
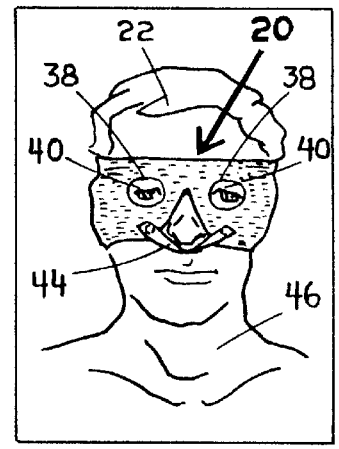
FIG. 4 shows a front view of the peri-orbital mask attached to the patient with the securing strap in place.

The peri-orbital mask 20 includes a first end 24, a second end 26, a top portion 28, a bottom portion 30 and a center section 32. In the bottom portion 30 of the center section 32 is an inverted "V"-shaped groove 34. The groove 34 is adapted for receipt around a portion of a patient's nose 36 as shown in FIGS. 3–5. The center section 32 of the peri-orbital mask 20 also includes a pair of eye openings 38 for receipt in front of the patient's eyes 40 shown in FIGS. 4 and 5.

In this drawing, the first end 24 is shown with a pair of round hook fasteners 42. The mask 20 also includes a securing strap 44 having a pair of round hook fasteners 42 attached at opposite ends of the strap 44. The strap 44, using the fasteners 42 is releasably attached to opposite sides of the groove 34.

Figure 2:
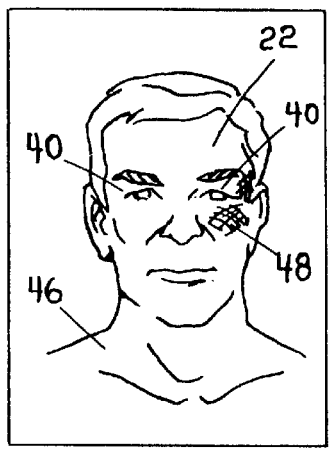
FIG. 2 shows the nature of the facial tissue injury to a patient that can benefit from use of the peri-orbital mask

In FIG. 2, a patient 46 is shown with a typical peri-orbital facial injury 48. The peri-orbital mask 20 is designed to accommodate an injury to this part of the face. The benefit to the patient 46 is to not be unnecessarily burdened with wearing excessive facial mask material.

In FIG. 3, an installation of the peri-orbital mask 20 around the peri-orbital patient's head 22 is shown. The first end 24 of the peri-orbital mask 20 is positioned for releasable attachment to the second end 26 using the hook fasteners 42. It should be noted that the mask material is made of a stretchable loose weave material. This loose weave material is also breathable, washable and reusable. Also of importance is that the loose weave material of the mask 26 provides for loop fasteners when the hook fasteners 42 are placed thereon. This feature allows for infinite adjustment when securing the mask to various sizes and shapes of heads.

In FIG. 4, a front view of the peri-orbital mask 20 is shown attached to the patient's head 22. The securing strap 42 is shown in place attached to the sides of the "V" -shaped groove 34 using the hook fasteners 42 that releasably attach to the loose weave mask material.

In FIG. 5, a perspective view of the patient 46 and the mask 20 received thereon is shown. Note that the peri-orbital mask 20 can also accommodate an eye injury by placing a sterile gauze pad next to either of the eye openings 38.

Figure 6:
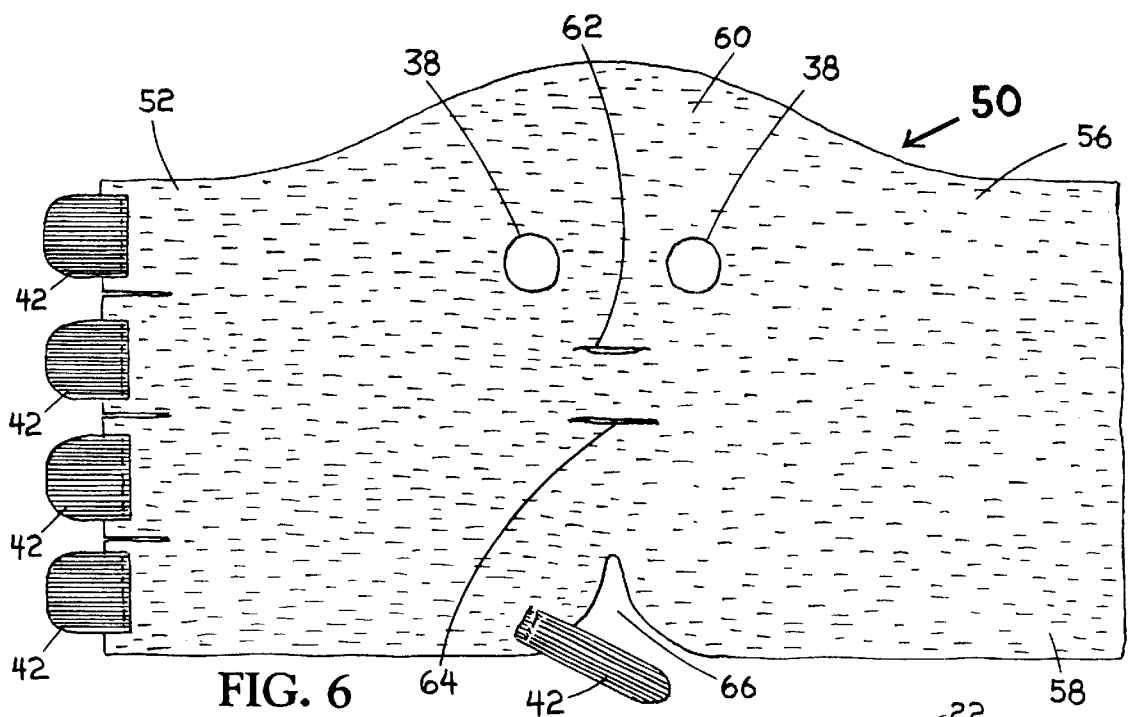
FIG. 6 is a flat pattern layout of a full-face mask with a chin hook fastener detached on one end to facilitate installation. A left end of the mask shows four hook fasteners that attach to a right end of the mask when secured around the patient's head. A center section of the mask shows openings for the eyes, nose, and mouth.

In FIG. 6, a flat pattern layout of the full-face mask is shown. The full-face mask has a general reference numeral 50. The full-face mask 50 includes a first end 52, a second end 54, a top portion 56, a bottom portion 58 and a center section 60. The center section 60 of the full-face mask 50 has a pair of eye openings 38 adapted for receipt in front of the patient's eyes 40. Also, the center section 60 includes a nose opening 62 and a mouth opening 64 adapted to allow the patient 46 to breathe and eat while wearing the full-face mask 50. In the bottom portion 58 of the center section 60 is a chin inverted "V" groove 66 with an elongated hook fastener 42 attached to one side of the groove 66. The groove 66 allows the lower portion 58 of the mask 50 to wrap around the bottom of the patient's chin and releasably attached to an opposite side of the groove 66.

A set of four hook fasteners 42 are shown attached to the first end 52 of the mask 50. The fasteners 42 are used for releasable attachment to the loose weave material of the second end 54 of the full-face mask 50.

Figure 7:
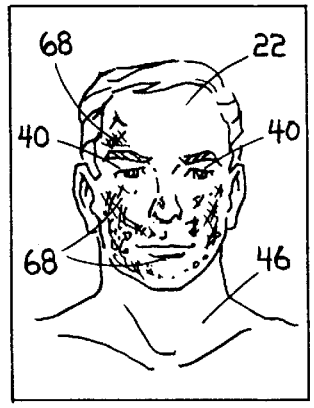
FIG. 7 shows the nature of the facial tissue injury to a patient that can benefit from use of the full-face mask.

In FIG. 7, the patient 46 is shown with a typical full-face injury 68, which the fullface mask 50 is designed to accommodate.

Figure 8:
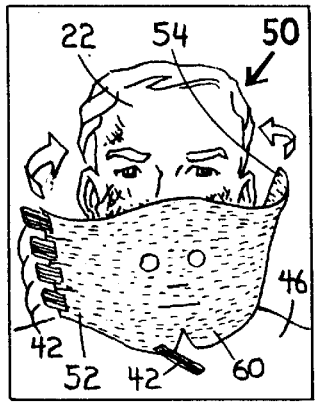
FIG. 8 shows the installation of the full-face mask around the patient's head with the ends of the mask positioned to attach at the rear of the patient's head.

In FIG. 8, installation of the full-face mask 50 around the patient's head 22 is shown. In this view, the fasteners 42 attached to the first end 52 are shown positioned for releasable attachment to the second end 54 of the full face mask 50 at the rear of the patient's head 22.

Figure 9:
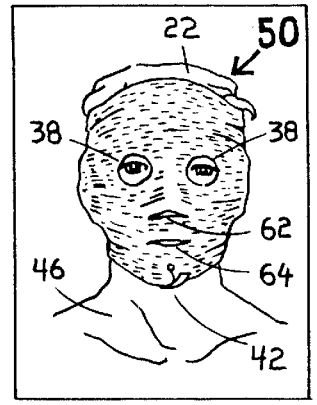
FIG. 9 shows a front view of the full-face mask attached to the patient with the securing strap in place.

In FIG. 9, a front view of the full-face mask 50 is shown attached to the patient's head 22. Note the elongated fastener 42 is attached in place closing the groove 66 and helping contour the bottom portion 58 of the mask 50 around the patient's chin.

Figures 10, 11:
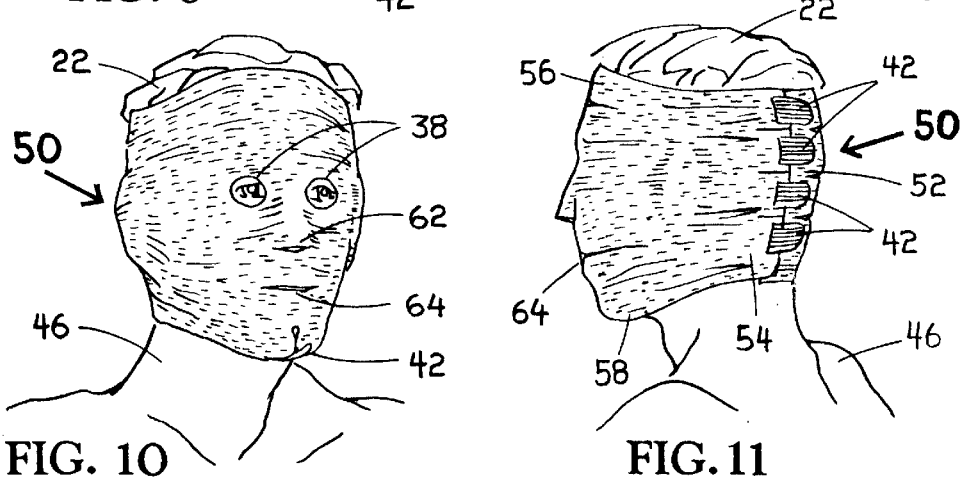
FIG. 10 is a front perspective view of the full-face mask attached to the patient with the chin hook fastener in place.
FIG. 11 is a rear perspective view of the full-face mask of FIG. 6 in use and fully attached to the patient with the chin hook fastener in place and the four rear hook fasteners attached at the back of the patient's head.

In FIG. 10, a front perspective view of the mask 50 is shown. Note the top portion 56 in the center section 60 of the mask 50 is curved upwardly. This curved portion is designed to cover the forehead of the patient 46.

In FIG. 11, a rear perspective view of the full-face mask is shown mounted on the patient's head 22. The hook fasteners 42 of the first end 52 are shown releasably engaged to the second end 54 of the full-face mask 50 to hold the full-face mask in place on the patient's head 22.

Figure 12:
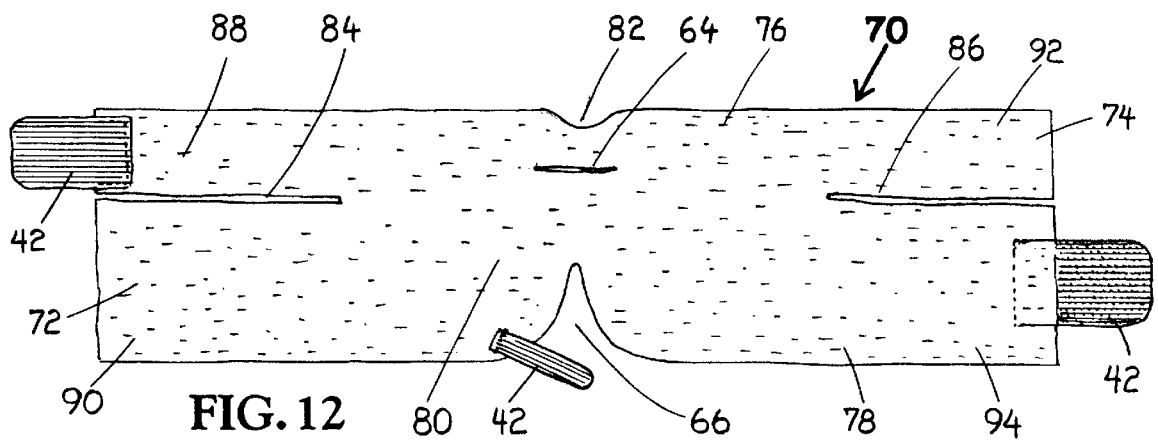
FIG. 12 is a flat pattern layout of a peri-oral mask with a chin hook fastener detached on one end to facilitate installation. A right end of the mask shows a top hook fastener used to attach the mask to the top of the head. A left end of the mask shows an upper rear hook fastener used to attach the mask to the rear of the head. Horizontal relief slits are shown on the left and right ends of the mask to facilitate the hook fastener attachments, to the loose weave nature of the material at both the rear of the patients head and the top of the patients head. A center of the mask has an opening for the mouth, an upper relief groove for the bottom of the nose, and a lower relief groove to facilitate the chin hook fasteners securing the mask around the bottom of the chin.

In FIG. 12, a flat pattern layout of the peri-oral mask 70 is shown. The peri-oral mask 70 includes a first end 72, a second end 74, a top portion 76, a bottom portion 78, and a center section 80. The center section 80 of the peri-oral mask 70 has a chin inverted "V" groove 66, and a nose groove 82 in the top portion 76 for fitting next to the bottom of the nose 36. The first end 72 of the mask 70 includes a hook fastener 42 and a first horizontal slit 84 in the top portion 76. The second end 74 also includes a second horizontal slit 86. The first horizontal slit 84 divides the first end 72 into an upper first horizontal headband 88 and a lower first folded vertical headband 90. The second horizontal slit 86 divides the second end 74 into an upper second horizontal headband 92 and a lower second folded vertical headband 94. In this drawing and in FIGS. 14–16, the mask 70 is shown having a mouth opening 64 similar to the mouth opening 64 shown in FIGS. 6 and 9–11.

Figure 13:
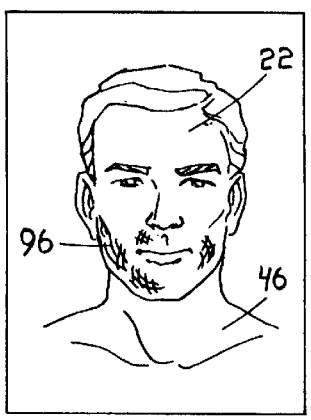
FIG. 13 shows the nature of a facial tissue injury to the patient that can benefit from use of the peri-oral mask.

In FIG. 13, the patient 46 is shown with a typical peri-oral facial injury 96 which the peri-oral mask 70 is designed to accommodate.

Figure 14:
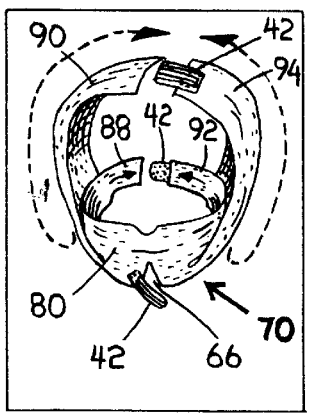
FIG. 14 shows the installation of the peri-oral mask around the patient's head, which is removed from the view for clarity. The rear and top hook fasteners are shown attached to the mask material to the head are shown with the chin hook tab left unattached.

In FIG. 14, the wrapping of the peri-oral mask 70 is shown. The patient's head 22 is not shown in this drawing. In this view, the first and second horizontal headbands 88 and 92 are in position for attachment to each other using the hook fastener 42. Also, the first and second vertical headbands 90 and 94 have been folded upwardly and are in position for attachment to each other using the hook fastener 42.

Figure 15:
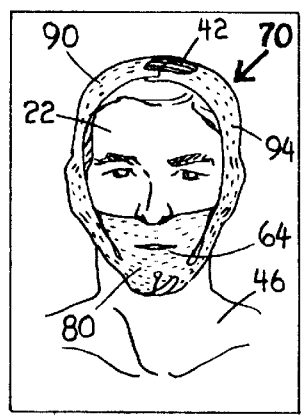
FIG. 15 shows a front view of the peri-oral mask attached to the patient with the chin hook fastener securing a lower portion of the mask in place. Also the hook fastener attachment at the top of the head is shown.

In FIG. 15, a front view of the peri-oral mask 70 is shown received on and around the patient's head 22.

Figure 16:
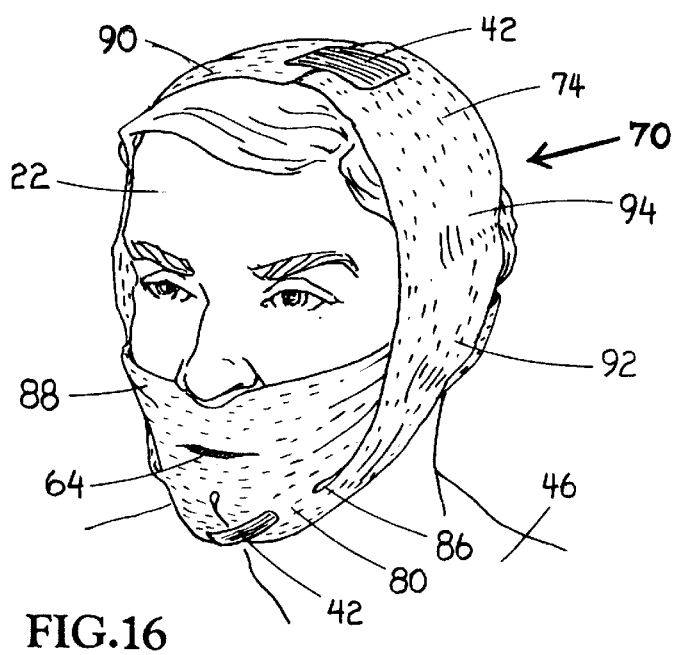
FIG. 16 is a front perspective view of the peri-oral mask shown in FIG. 12. The mask is fully attached to the patient at three different points on the patient. The points are the chin, the top of the head, and the rear of the head.

In FIG. 16, a front perspective view of the peri-oral mask 70 is shown. The center section 80 is received in front of the patient's mouth and chin with the nose groove 82 received under the patient's nose. The fastener 42 has been used to secure the opposite sides of the inverted "V" groove 66 for contouring the bottom portion 78 of the mask 70 around the patient's chin.

In this drawing, the first horizontal headband 88 and the second horizontal headband 92 can be seen wrapped around the sides of the patient's head 22 and secured together at the back of the head. Also, the first vertical headband 90 and the second vertical headband 94 are shown folded upward and secured together using the fastener 42 at the top of the head.

While the invention has been particularly shown, described and illustrated in detail with reference to the preferred embodiments and modifications thereof, it should be understood by those skilled in the art that equivalent changes in form or detail may be made therein without departing from the true spirit and scope of the invention as claimed, except as precluded by the prior art.

The embodiments of the invention for which an exclusive privilege and property right is claimed are defined as follows:

1. A peri-oral facial wound dressing support device configured to accommodate a peri-oral facial injury and expedite the healing process while minimizing a patient's facial discomfort, the device adaptable for conforming to a patient's head and face, the device comprising:
   an elongated mask made of loose weave material and having a top portion, a bottom portion, a first end, a second end and a center section,
      the first end having a first slit therein and along a portion of a length of said mask, said first slit dividing the first end into an upper first horizontal headband and a folded lower first vertical headband,
      the second end having a second slit therein and along a portion of the length of said mask, said second slit dividing the second end into an upper second horizontal headband and a folded lower second vertical headband;
   a mouth opening in the center section of said mask;
   a first non-adhesive fastener disposed on a portion of a first end of said first horizontal headband, said first fastener releasably engaging the loose weave material along a length of a portion of a second end of said second horizontal headband for infinite adjustment thereon; and
   a second non-adhesive fastener disposed on a portion of a second end of said folded second vertical headband, said second fastener releasably engaging the loose weave material along a length of a portion of a first end of said folded first vertical headband for infinite adjustment thereon.

2. The device as described in claim 1 wherein said first fastener is a hook fastener attached to the first end of said first horizontal headband, said first hook fastener for releasably engaging the loose weave material along a length of the second end of said second horizontal headband for infinite adjustment thereon.

3. The device as described in claim 1 wherein said second fastener is a hook fastener attached to the second end of said folded second vertical headband, said second hook fastener for releasably engaging the loose weave material along a length of the first end of said folded vertical headband for infinite adjustment thereon.

4. The device as described in claim 1 further including a chin inverted "V" groove in the bottom portion of the center section of said mask and a chin hook fastener attached to a side of said chin groove, said chin groove and chin hook fastener adapted for securing a portion of said mask around the patient's chin.

5. The device as described in claim 1 further including a nose groove in the top portion of the center section of said mask and adapted for receipt under the patient's nose.

6. The device as described in claim 1 wherein said mask is made of a stretchable, breathable, washable and reusable material.

7. A peri-oral facial wound dressing support device configured to accommodate a peri-oral facial injury and expedite the healing process while minimizing a patient's facial discomfort, the device adaptable for conforming to a patient's head and covering a lower third of the patient's face, the device comprising:

an elongated mask made of loose weave material and having a top portion, a bottom portion, a first end, a second end and a center section, the first end having a first slit therein and along a portion of a length of said mask, said first slit dividing the first end into an upper first horizontal headband and a folded lower first vertical headband, the second end having a second slit therein and along a portion of the length of said mask, said second slit dividing the second end into an upper second horizontal headband and a folded lower second vertical headband;

a mouth opening in the center section of said mask;

a first hook fastener disposed on a portion of a first end of said first horizontal headband of said mask, said first hook fastener releasably engaging the loose weave material along a length of a portion of a second end of said second horizontal headband for infinite adjustment thereon; and a second hook fastener disposed on a portion of a second end of said folded second vertical headband, said second hook fastener releasably engaging the loose weave material along a length of a portion of a first end of said folded first vertical headband for infinite adjustment thereon.

8. The device as described in claim 7 further including a chin inverted "V" groove in the bottom portion of the center section of said mask and a chin hook fastener attached to a side of said chin groove, said chin groove and chin hook fastener adapted for securing a portion of the mask around a portion of the patient's chin.

9. The device as described in claim 7 further including a nose groove in the top portion of the center section of said mask and adapted for receipt under the patient's nose.

10. The device as described in claim 7 wherein said mask is made of a stretchable, breathable, washable and reusable material.

* * * * *